(12) United States Patent
O'Reagan et al.

(10) Patent No.: US 7,314,462 B2
(45) Date of Patent: Jan. 1, 2008

(54) PASSIVE NEEDLE-STICK PROTECTOR (75) Inventors: James O'Reagan, Greer, SC (US); Douglas Kennemore, Greenville, SC (US)

(73) Assignee: Span-America Medical Systems, Inc., Greenville, SC (US)

( * ) Notice: Subject to any disclaimer, the term of this patent is extended or adjusted under 35 U.S.C. 154(b) by 451 days.

(21) Appl. No.: 11/103,701

(22) Filed: Apr. 12, 2005

(65) Prior Publication Data

US 2006/0229563 A1 Oct. 12, 2006

(51) Int. Cl.
*A61M 5/178* (2006.01)
*A61M 5/00* (2006.01)

(52) U.S. Cl. .................. 604/164.08; 604/110

(58) Field of Classification Search ............... 604/93.1, 604/110, 164, 164.01, 164.08, 187, 198, 264, 604/272, 508
See application file for complete search history.

(56) References Cited

U.S. PATENT DOCUMENTS

| | | | |
|---|---|---|---|
| 2,712,453 A * | 7/1955 | Dion | ................. 280/763.1 |
| 4,211,741 A | 7/1980 | Ostoich | |
| 4,254,773 A | 3/1981 | Waldbillig | |
| 4,391,029 A | 7/1983 | Czuba et al. | |
| 4,424,833 A | 1/1984 | Spector et al. | |
| 4,588,398 A | 5/1986 | Daugherty et al. | |
| 4,661,300 A | 4/1987 | Daugherty | |
| 4,664,657 A | 5/1987 | Williamitis et al. | |
| 4,683,916 A | 8/1987 | Raines | |
| 4,713,057 A | 12/1987 | Huttner et al. | |
| 4,728,322 A | 3/1988 | Walker et al. | |
| 4,781,703 A | 11/1988 | Walker et al. | |
| 4,801,295 A | 1/1989 | Spencer | |
| 4,832,696 A | 5/1989 | Luther et al. | |
| 4,846,805 A | 7/1989 | Sitar | |
| 4,850,961 A | 7/1989 | Wanderer et al. | |
| 4,883,699 A | 11/1989 | Aniuk et al. | |
| 4,917,669 A | 4/1990 | Bonaldo | |
| 4,944,728 A | 7/1990 | Carrell et al. | |
| 4,952,207 A | 8/1990 | Lemieux | |
| 5,000,736 A | 3/1991 | Kaufhold, Jr. et al. | |
| 5,000,740 A | 3/1991 | Ducharme et al. | |
| 5,013,304 A | 5/1991 | Russell et al. | |
| 5,019,049 A | 5/1991 | Haining | |
| 5,051,109 A | 9/1991 | Simon | |
| 5,088,985 A | 2/1992 | Deras | |
| 5,088,986 A | 2/1992 | Nusbaum | |
| 5,088,987 A | 2/1992 | Noonan, Jr. | |
| 5,088,988 A | 2/1992 | Talonn et al. | |
| 5,092,845 A | 3/1992 | Chang | |
| 5,092,853 A | 3/1992 | Couvertier, II | |
| 5,102,394 A | 4/1992 | Lasaitis et al. | |
| 5,108,374 A | 4/1992 | Lemieux | |
| 5,127,905 A | 7/1992 | Lemieux | |
| 5,135,504 A | 8/1992 | McLees | |
| 5,171,230 A | 12/1992 | Eland et al. | |
| 5,171,231 A | 12/1992 | Heiliger | |

(Continued)

*Primary Examiner*—Samchuan C. Yao
*Assistant Examiner*—William Carpenter
(74) *Attorney, Agent, or Firm*—Drinker Biddle & Reath LLP (57) ABSTRACT

The present invention relates to a needle-stick protector for an intravenous catheter having a body, a needle hub, a needle, and means for ensuring that the needle-stick protector is not removed from a catheter hub before the needle is fully retracted and locked in the body of the needle-stick protector.

10 Claims, 9 Drawing Sheets

U.S. PATENT DOCUMENTS

| | | |
|---|---|---|
| 5,176,650 A | 1/1993 | Haining |
| 5,183,469 A | 2/1993 | Capaccio |
| 5,188,597 A | 2/1993 | Sweeney et al. |
| 5,188,607 A | 2/1993 | Wu |
| 5,201,713 A | 4/1993 | Rosetti |
| 5,215,525 A | 6/1993 | Sturman |
| 5,215,527 A | 6/1993 | Beck et al. |
| 5,215,528 A | 6/1993 | Purdy et al. |
| 5,219,333 A | 6/1993 | Sagstetter et al. |
| 5,222,947 A | 6/1993 | D'Amico |
| 5,226,899 A | 7/1993 | Lee et al. |
| 5,234,416 A | 8/1993 | Macaulay et al. |
| 5,240,537 A | 8/1993 | Bodicky |
| 5,242,393 A | 9/1993 | Brimhall et al. |
| 5,250,034 A | 10/1993 | Appling et al. |
| 5,250,066 A | 10/1993 | Lambert |
| 5,254,107 A | 10/1993 | Soltesz |
| 5,261,885 A | 11/1993 | Lui |
| 5,267,971 A | 12/1993 | Brimhall |
| 5,267,979 A | 12/1993 | Appling et al. |
| 5,273,543 A | 12/1993 | Bell et al. |
| 5,279,590 A | 1/1994 | Sinko et al. |
| 5,279,591 A | 1/1994 | Simon |
| 5,300,048 A | 4/1994 | Drewes, Jr. et al. |
| 5,304,136 A | 4/1994 | Erskine et al. |
| 5,304,140 A | 4/1994 | Kugo et al. |
| 5,304,144 A | 4/1994 | Brimhall |
| 5,304,149 A | 4/1994 | Morigi |
| 5,304,155 A | 4/1994 | Lui |
| 5,306,253 A | 4/1994 | Brimhall |
| 5,308,330 A | 5/1994 | Grimard |
| 5,312,361 A | 5/1994 | Zadini et al. |
| 5,312,371 A | 5/1994 | Dombrowski et al. |
| 5,316,706 A | 5/1994 | Muni et al. |
| 5,318,547 A | 6/1994 | Altschuler |
| 5,328,473 A | 7/1994 | Fayngold et al. |
| 5,334,144 A | 8/1994 | Alchas et al. |
| 5,338,310 A | 8/1994 | Lewandowski |
| 5,342,309 A | 8/1994 | Hausser |
| 5,344,404 A | 9/1994 | Benson |
| 5,344,408 A | 9/1994 | Partika |
| 5,356,390 A | 10/1994 | Erskine |
| 5,370,624 A | 12/1994 | Edwards et al. |
| 5,376,073 A | 12/1994 | Graves et al. |
| 5,380,298 A | 1/1995 | Zabetakis et al. |
| 5,380,307 A | 1/1995 | Chee et al. |
| 5,385,554 A | 1/1995 | Brimhall |
| 5,385,555 A | 1/1995 | Hausser |
| 5,395,341 A | 3/1995 | Slater |
| 5,397,512 A | 3/1995 | Sloane, Jr. et al. |
| 5,405,323 A | 4/1995 | Rogers et al. |
| 5,405,326 A | 4/1995 | Haber et al. |
| 5,407,431 A | 4/1995 | Botich et al. |
| 5,409,461 A | 4/1995 | Steinman |
| 5,409,463 A | 4/1995 | Thomas et al. |
| 5,409,644 A | 4/1995 | Martin et al. |
| 5,411,486 A | 5/1995 | Zadini et al. |
| 5,415,184 A | 5/1995 | Peck |
| 5,417,668 A | 5/1995 | Setzer et al. |
| 5,419,766 A | 5/1995 | Chang et al. |
| 5,419,777 A | 5/1995 | Hofling |
| 5,423,758 A | 6/1995 | Shaw |
| 5,423,766 A | 6/1995 | Di Cesare |
| 5,423,773 A | 6/1995 | Jimenez |
| 5,425,712 A | 6/1995 | Goodin |
| 5,425,735 A | 6/1995 | Rosen et al. |
| 5,425,903 A | 6/1995 | Sloane, Jr. et al. |
| 5,429,613 A | 7/1995 | D'Amico |
| 5,429,617 A | 7/1995 | Hammersmark et al. |
| 5,435,314 A | 7/1995 | Dias |
| 5,437,648 A | 8/1995 | Graves et al. |
| 5,441,489 A | 8/1995 | Utsumi et al. |
| 5,443,457 A | 8/1995 | Ginn et al. |
| 5,445,619 A | 8/1995 | Burns |
| 5,445,624 A | 8/1995 | Jimenez |
| 5,446,230 A | 8/1995 | Travers et al. |
| 5,447,501 A | 9/1995 | Karlsson et al. |
| 5,447,503 A | 9/1995 | Miller |
| 5,447,724 A | 9/1995 | Helmus et al. |
| 5,449,349 A | 9/1995 | Sallee et al. |
| 5,453,095 A | 9/1995 | Davila et al. |
| 5,453,099 A | 9/1995 | Lee et al. |
| 5,456,668 A | 10/1995 | Ogle, II |
| 5,456,674 A | 10/1995 | Bos et al. |
| 5,458,658 A | 10/1995 | Sircom |
| 5,462,533 A | 10/1995 | Daugherty |
| 5,464,398 A | 11/1995 | Haindl |
| 5,464,399 A | 11/1995 | Boettger |
| 5,472,430 A | 12/1995 | Vaillancourt et al. |
| 5,474,539 A | 12/1995 | Costa et al. |
| 5,478,313 A | 12/1995 | White |
| 5,478,328 A | 12/1995 | Silverman et al. |
| 5,487,732 A | 1/1996 | Jeffrey |
| 5,501,672 A | 3/1996 | Firth et al. |
| 5,520,654 A * | 5/1996 | Wahlberg .............. 604/164.08 |
| 5,531,701 A | 7/1996 | Luther |
| 5,562,631 A | 10/1996 | Bogert |
| 5,584,809 A * | 12/1996 | Gaba ......................... 604/110 |
| 5,853,393 A * | 12/1998 | Bogert .................. 604/165.02 |
| 6,032,369 A * | 3/2000 | Tada et al. .................... 30/276 |
| 6,080,137 A * | 6/2000 | Pike .......................... 604/263 |
| 6,749,588 B1 * | 6/2004 | Howell et al. ......... 604/164.08 |

* cited by examiner

PASSIVE NEEDLE-STICK PROTECTOR

FIELD OF THE INVENTION

This invention pertains to a needle-stick protector for an intravenous catheter. More specifically, the invention is directed to a needle-stick protector having a body, a needle hub, a needle, and means for ensuring that the needle is retracted and locked in the body before the needle-stick protector is disengaged from the catheter.

BACKGROUND OF THE INVENTION

Intravenous catheters are medical devices for administering intravenous fluids, medications, and blood products. An intravenous catheter generally consists of a hollow-bore needle and a close-fitting, over the needle plastic catheter tubing used to access the lumen of a blood vessel in a patient. After the needle and catheter are inserted into the blood vessel, the needle is retracted from the patient and discarded, leaving only the catheter in the blood vessel. The distal end of the catheter contains a catheter hub through which fluids, medications, and blood may be injected or through which blood samples may be taken from the patient. When the needle is removed from the catheter, the pointed end of the needle can be accidentally poked into the person handling the needle or someone in the vicinity of the needle. Any residual blood on the needle can be inserted in the person poked by the needle thereby transmitting microorganisms, e.g., bacteria and viruses, usually referred to collectively as blood-borne pathogens.

In order to prevent accidental pokes, needle-stick protectors have been designed to capture the needle as it is being withdrawn from the catheter. One such needle-stick protector is illustrated in U.S. Pat. No. 6,080,137, incorporated herein by reference. However, present needle-stick protectors rely on the user operating the device correctly. If a needle is not properly locked in the needle-stick protector, the needle may exit the protector and accidentally poke the user. Therefore, a need exists for a needle-stick protector having a means that ensures that the pointed, contaminated end of the needle can never be exposed to the user during the extraction and disposal of the needle.

SUMMARY OF THE INVENTION

The present invention relates to a needle-stick protector for an intravenous catheter wherein the needle-stick protector is attached to a catheter hub by a luer lock engagement. The needle-stick protector of the present invention includes a body, a needle hub, a needle, and means for ensuring that the needle-stick protector is not removed from a catheter hub before the needle is fully retracted and locked in the body of the needle-stick protector. The body has a first end and a second end and includes a plurality of side walls extending between the first and second ends in a geometric configuration. The side walls define an interior space and at least two slots. The needle hub having a front end, a back end, a first side, and a second side is positioned in the interior space of the body. The front end of the needle hub is adapted to receive a needle. The first and second sides of the needle hub each includes a handle. The handles extend through the slots of the body to positions outside of the body. Movement of the handles of the needle hub causes corresponding movement of the needle. Therefore, when the handles are moved from the first end of the body to the second end of the body along the slots of the body, the needle moves from the exterior of the body into the interior space defined by the body. Accordingly, the needle is fully contained in the body before the needle-stick protector is removed from the catheter hub, thereby preventing accidental needle sticks. The needle-stick protector of the present invention further includes means for preventing movement of the luer lock engagement that connects the needle-stick protector to the catheter hub until the needle is securely locked in the body of the needle-stick protector.

DETAILED DESCRIPTION OF THE INVENTION

The needle-stick protector of the present invention includes a safety feature that provides "passive protection" to the user. "Passive protection" means that the user cannot misuse the safety feature, i.e., the user cannot forget to make sure the needle is locked into the needle-stick protector after withdrawing the needle from the catheter. The safety feature of the present invention is "passive" because the user does not have to deviate from the standard procedure in order to achieve needle-stick safety. The safety feature of the present invention includes any means that prevents movement of the luer lock engagement of a needle-stick protector and a catheter hub until the needle is fully retracted and locked in the body of the needle-stick protector.

Needle-stick protectors of the present invention are attached to a catheter hub using a luer lock engagement. The luer lock engagement comprises threads on the outside wall of the catheter hub engaged by threads located inside the opening of the needle-stick protector that attaches to the catheter hub. Needle-stick protectors not having the safety feature of the present invention are disengaged from the catheter hub by simply rotating the luer lock engagement counter-clockwise until the needle-stick protector is released from the catheter hub. The safety feature of the present invention prevents the disengagement of a needle-stick protector from a catheter hub until the needle is safety locked back into the body of the needle-stick protector by preventing the luer lock engagement from rotating until the needle is securely locked in the body of the needle-stick protector. By providing a means for connecting the locking mechanism for the needle in the body of a needle-stick protector with the luer lock engagement, the needle-stick protector cannot be released from the catheter hub until the needle is locked into the locking mechanism.

The safety feature of the present invention includes a wire that extends along the length of the interior space of the body of a needle-stick protector. The wire has a first end and a second end, with the first end acting as a locking pin that engages a hole on both sides of the luer lock engagement. In one embodiment of the present invention, the first end of the wire just penetrates the luer lock engagement. In another embodiment of the present invention, the first end of the wire engages the entire luer lock engagement and just penetrates the catheter hub, but does not enter the internal chamber of the catheter hub. The second end of the wire forms an L-shaped pin and is located near the locking mechanism for the needle hub at the second end of the needle-stick protector. The wire may be made of any suitable material, preferably metal or plastic. As the needle hub is locked into the needle-stick protector, the wire is activated by the L-shaped pin near the locking mechanism and the wire disengages the locking pin from the luer lock engagement. When the locking pin is released from the luer lock engagement, the needle-stick protector can now be disengaged from the catheter hub by simply rotating the luer lock engagement counter-clockwise while separating the needle-protector from the catheter hub.

The preferred embodiments and best mode of the present invention will now be described in detail with reference being made to the drawings. The needle-stick protector of the present invention is indicated generally in the drawings by the reference number "10."

Figure 3:
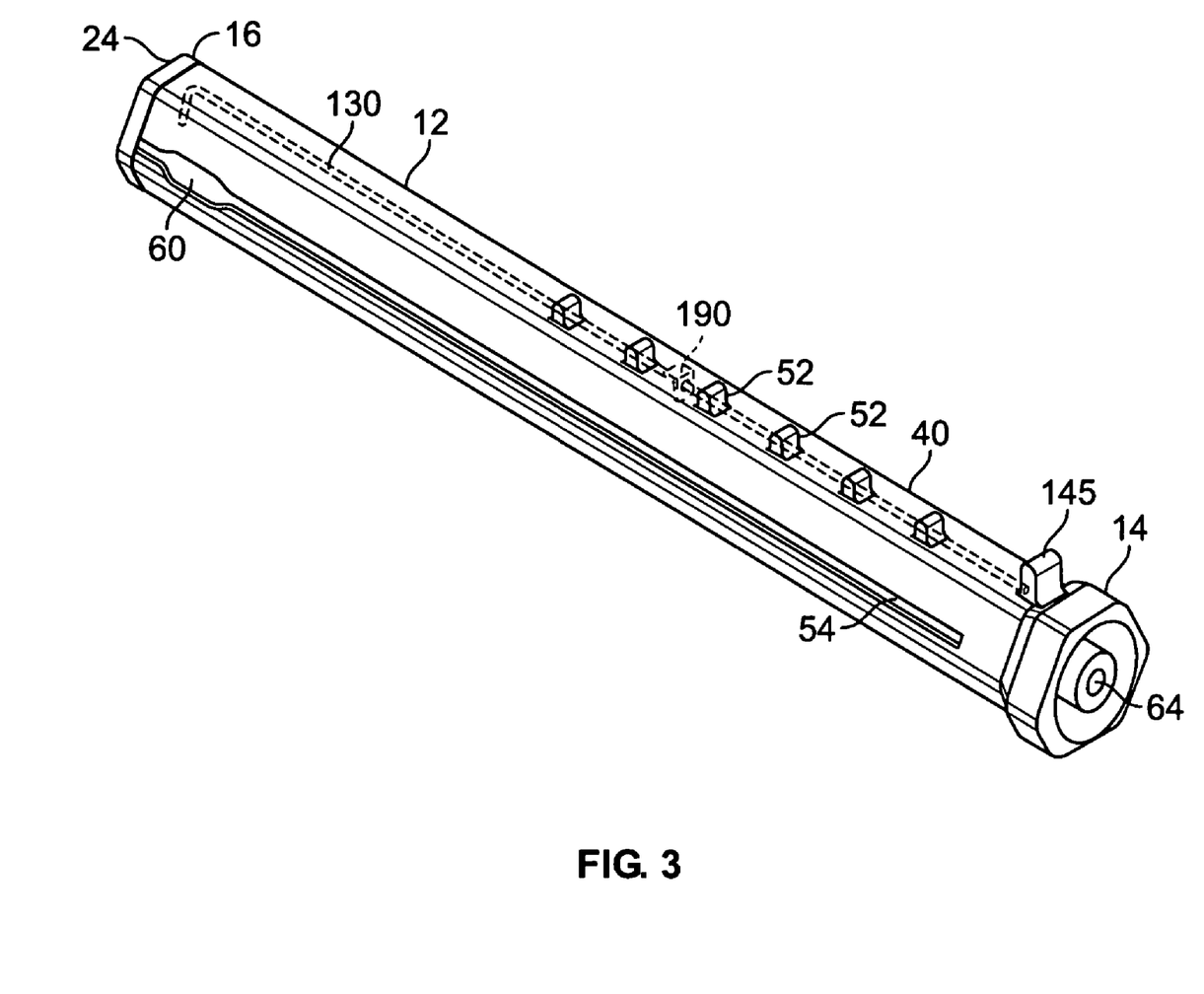
FIG. 3 is a perspective view of a needle-stick protector according to the present invention showing the needle-stick protector disengaged from a catheter hub.
Figure 4:
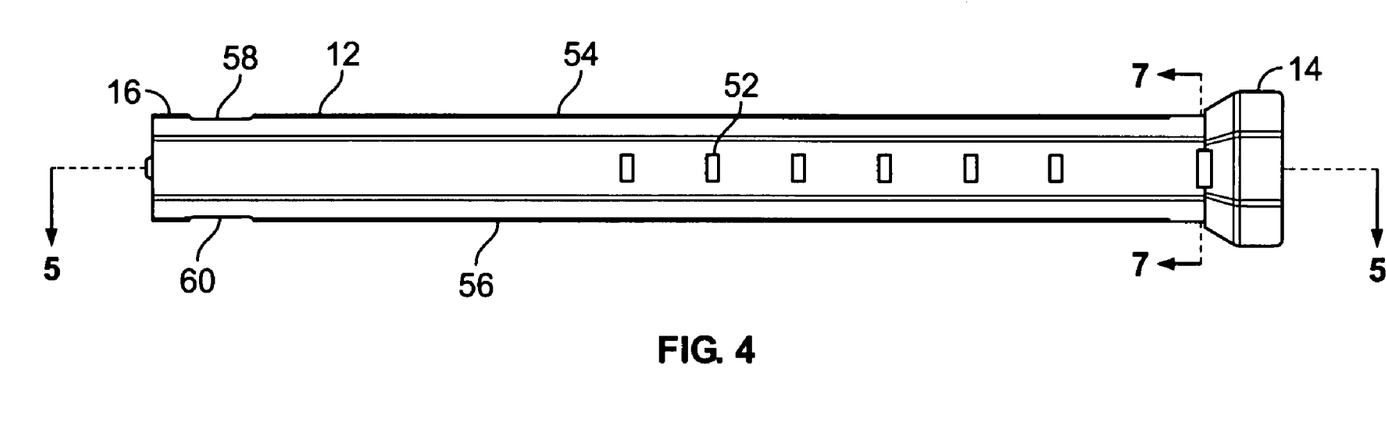
FIG. 4 is a top view of the body of the present needle-stick protector according to an embodiment of the present invention.
Figure 5:
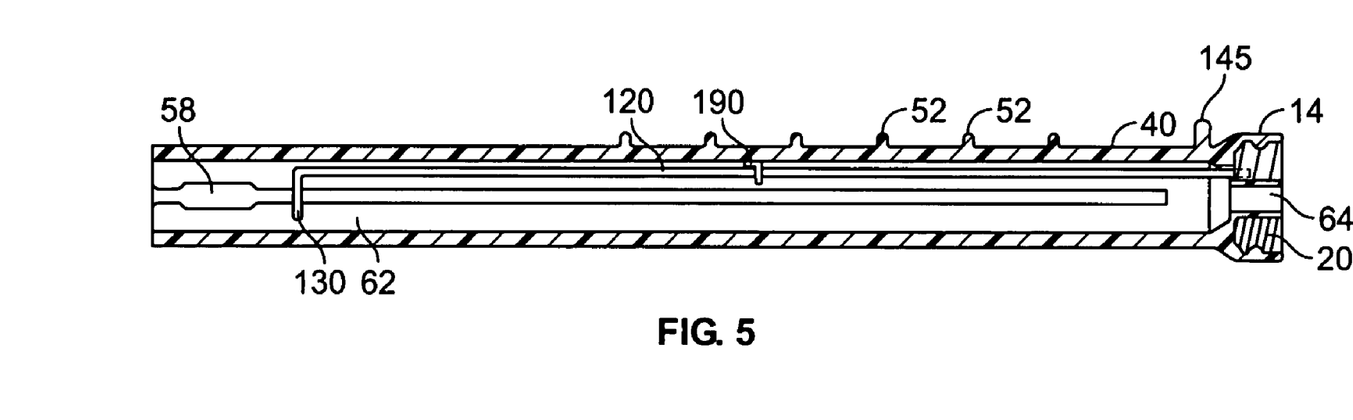
FIG. 5 is a cross-sectional view taken along line 5-5 of FIG. 4.
Figure 7:
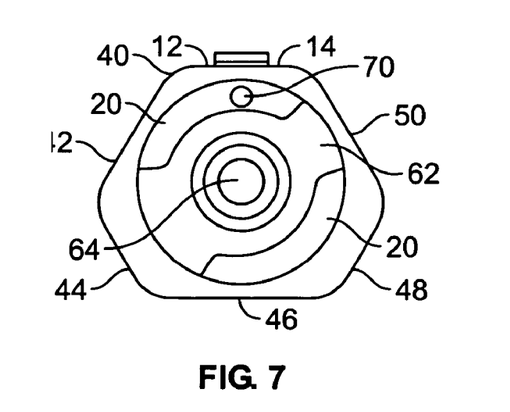
FIG. 7 is an elevational view of the first end of the body of the present needle-stick protector.

Referring to FIGS. 1-5, the needle-stick protector 10 includes a body 12 having a first end 14 and a second end 16. As shown in FIGS. 1, 2, 3 and 5, the first end 14 is adapted to receive a catheter hub 18. The first end 14 includes a plurality of threads 20, as shown in FIGS. 5 and 7, for receiving mating threads (not shown) positioned on the connection end 22 of the catheter hub 18. The mating of the threads 20 on the first end 14 of the body 12 with the threads (not shown) on the connection end 22 of the catheter hub 18 form a luer lock engagement 180 between the body 12 and the catheter hub 18. It should be understood that the first end 14 of the needle-stick protector 10 can be adapted to receive a variety of devices depending on the application. For the purpose of explanation, the catheter hub 18 shown in the present drawings will be used in conjunction with the needle-stick protector 10.

Figure 9:
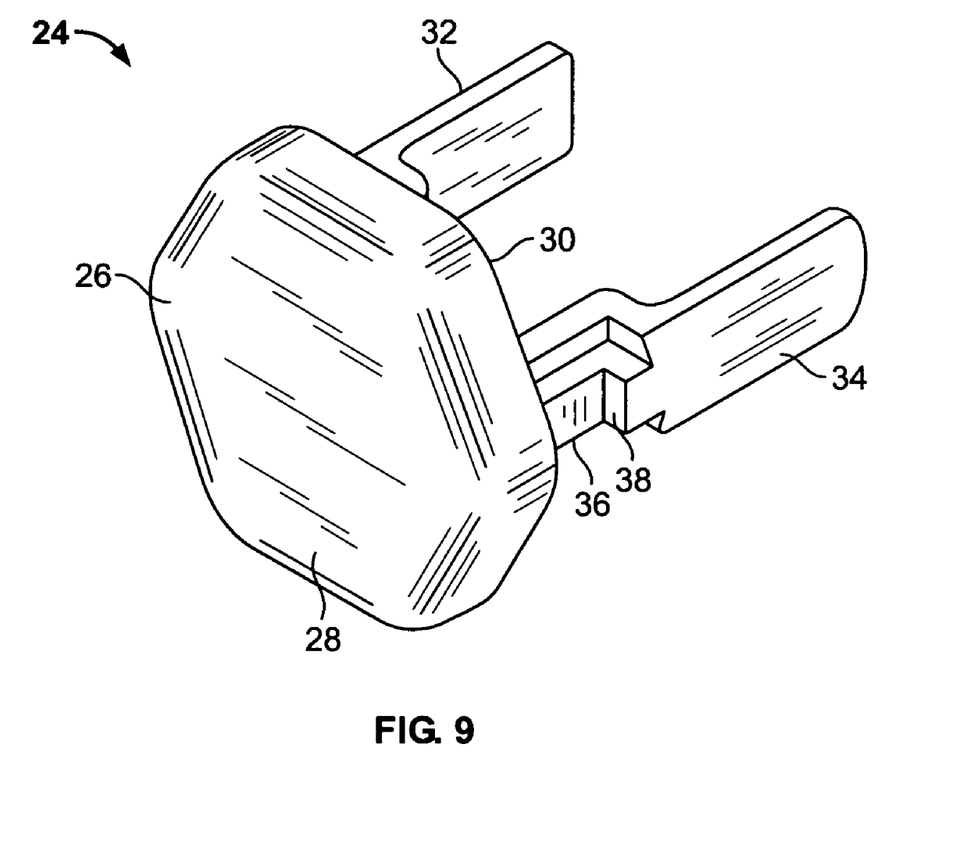
FIG. 9 is a perspective view of the end cap according to the present invention.

As shown in FIGS. 1B, 1C, 2 and 3, the second end 16 of the body 12 can be adapted to receive an end cap 24 shown in FIG. 9, having an exterior surface 28 and an interior surface 30. A first leg 32 and a second leg 34 extend outwardly from the interior surface 30 of a head 26. Each of the first and second legs 32 and 34 includes a locking recess 36 having a locking surface 38. The first and second legs 32 and 34 are inserted in the second end 16 of the body 12 to attach the cap 24 to the body.

Figure 2:
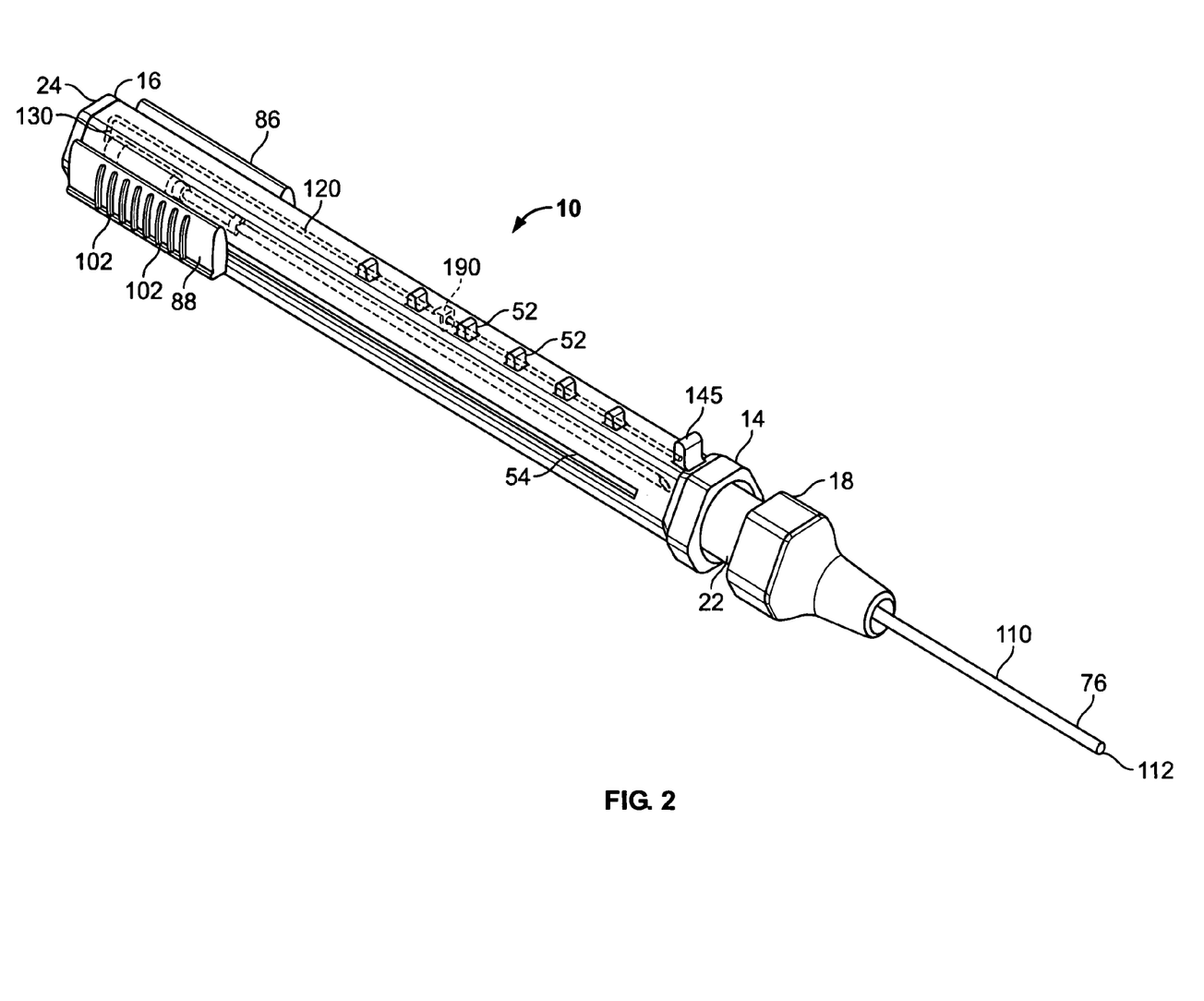
FIG. 2 is a perspective view of a needle-stick protector according to the present invention illustrating a needle fully retracted in the body of the needle-stick protector.

Referring to FIG. 3, the body 12 includes a plurality of side walls extending between the first end 14 and the second end 16 in a geometric configuration. It should be understood that the number of side walls of the body 12 can be changed to form various geometric configurations, such as square, circular, rectangular, polygonal, with a hexagonal configuration being preferred. As shown in FIGS. 1-5, a plurality of spaced upwardly extending projections 52 are positioned on a first side wall 40. A first projection or tab 145 on the first wall 40 is engaged by a finger of a user to accurately position the body 12 with respect to a blood vessel. The projections 52 may be engaged by the thumb to more accurately and easily handle the needle protector 10.

Referring to FIG. 4, the side walls of the body 12 define at least two slots. The first and second slots 54 and 56, respectively extend longitudinally between the first end 14 and the second end 16 of the body 12 in an opposed relationship to one another. As shown in FIGS. 3 and 4, the first and second slots 54 and 56 define first and second locking portions 58 and 60, respectively, adjacent the second end 16 of the body 12 in opposed relationship to one another. The first and second locking portions 58 and 60 are positioned adjacent to the locking recesses 36 of the first and second legs 32 and 34 of the end cap 24 depicted in FIG. 9.

Figure 10:
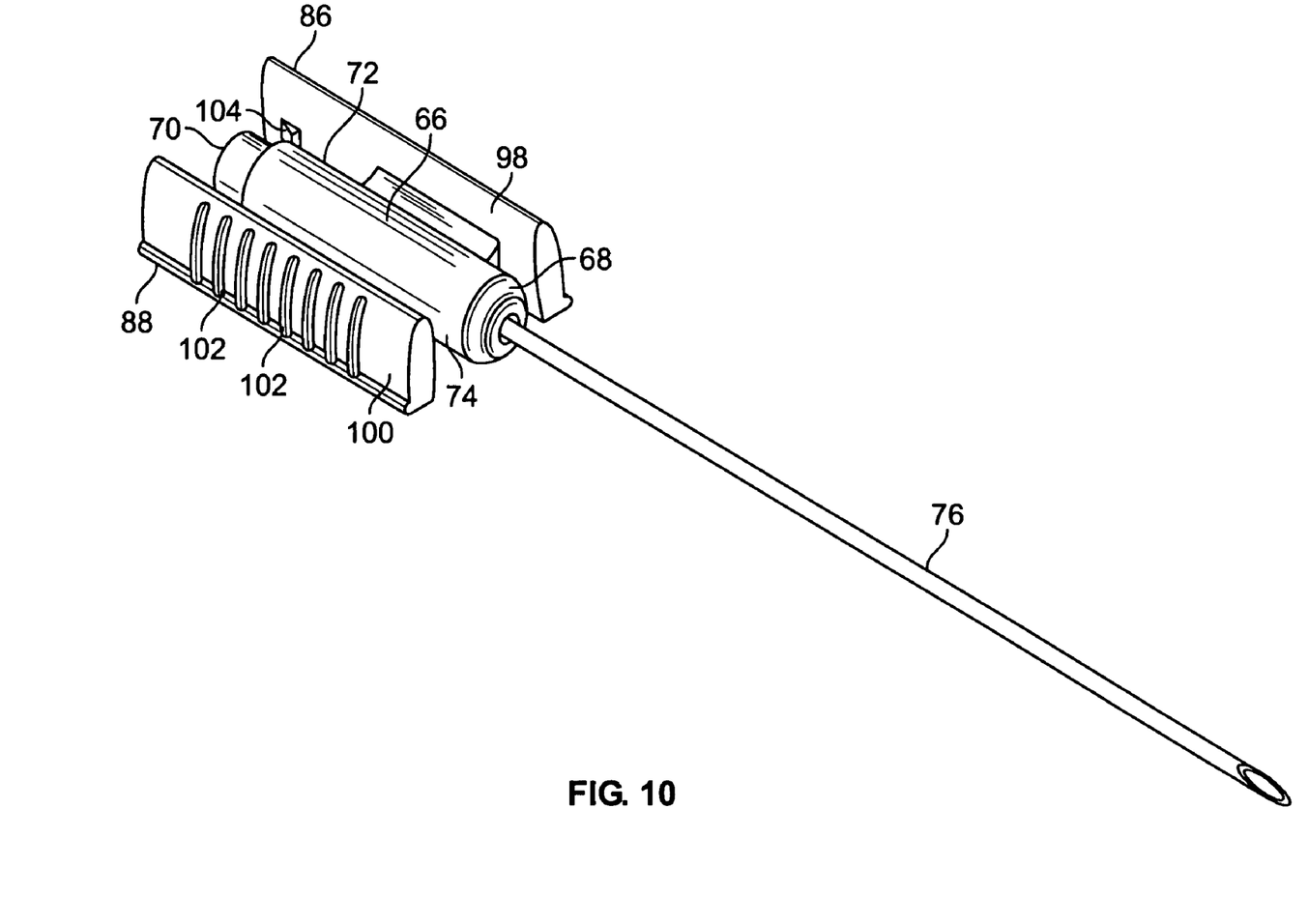
FIG. 10 is a perspective view of the needle hub and needle according to the present invention.
Figure 11:
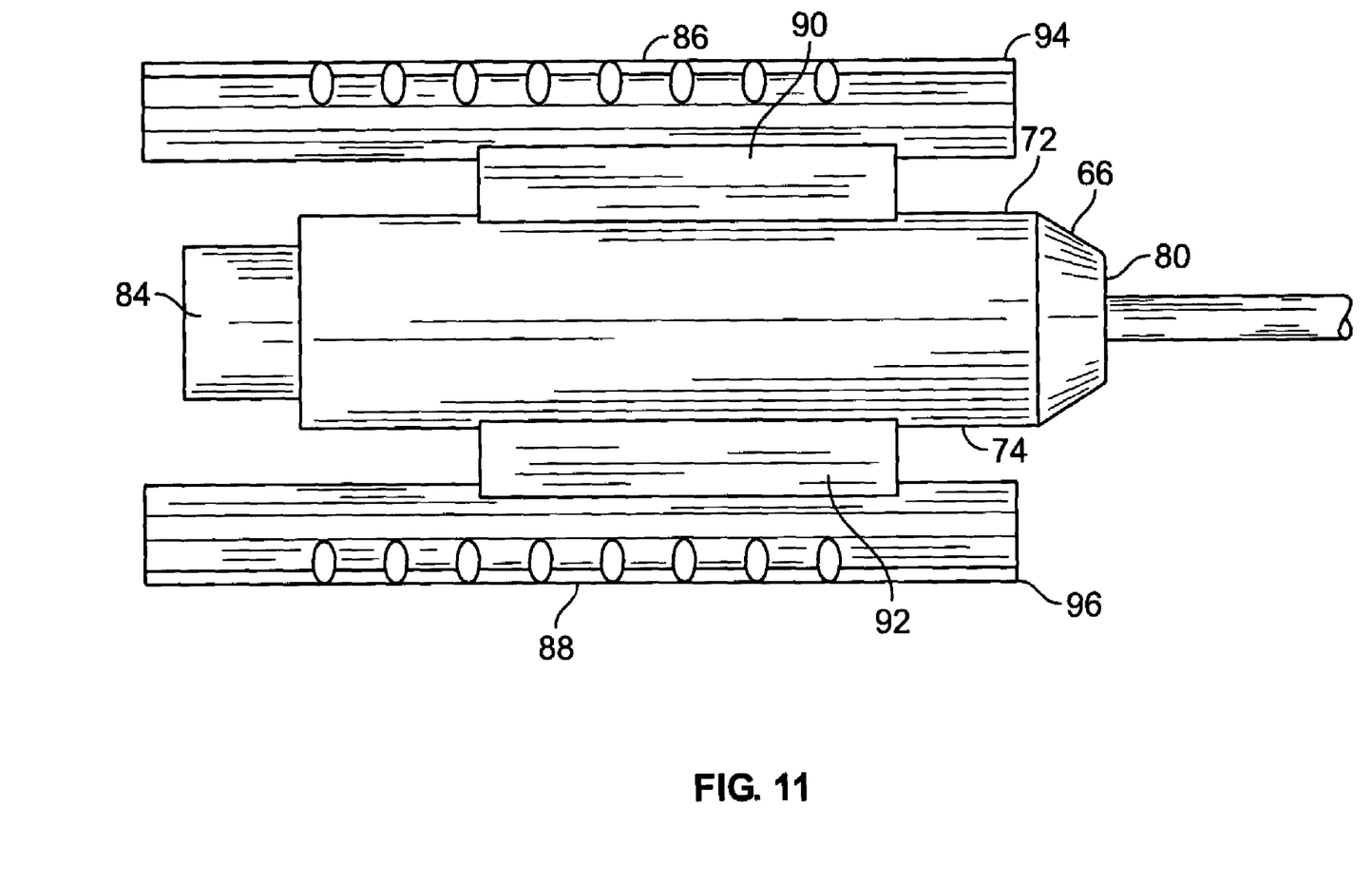
FIG. 11 is a top view of the needle hub according to the present invention.

Referring to FIGS. 10 and 11 the needle-stick protector 10 includes a needle hub 66 having a front end 68, a back end 70, a first side 72 and a second side 74. The needle hub 66 is movably positioned in an interior space 62 of the body 12. The front end 68 of the needle hub 66 is adapted to receive a needle 76. The front end 68 includes a front end opening 80 for receiving the needle 76. The first side 72 and the second side 74 of the needle hub 66 are adapted to receive first and second handles 86 and 88, respectively. The first and second handles 86 and 88 include first and second wings 90 and 92, respectively. The first and second wings 90 and 92 extend from the needle hub 66 through the first and second slots 54 and 56, respectively, to the exterior of the body 12.

Still referring to FIGS. 10 and 11, the first and second handles 86 and 88 include first and second handle members 94 and 96, respectively, attached to the first and second wings 90 and 92, respectively. Each of the first and second handle members 94 and 96 includes an interior surface 98 and an exterior surface 100. As shown in FIG. 10, each exterior surface 100 includes a plurality of spaced grips 102 as shown in FIG. 2. The grips 102 allow the first and second handles 86 and 88 to be firmly gripped during actuation of the needle hub 66. The first and second handle members 94 and 96 each includes a locking projection 104 extending inwardly from the interior surface 98. The locking projections 104 are received by the locking recesses 36 of the first and second legs 32 and 34 of the end cap 24.

Figure 6:
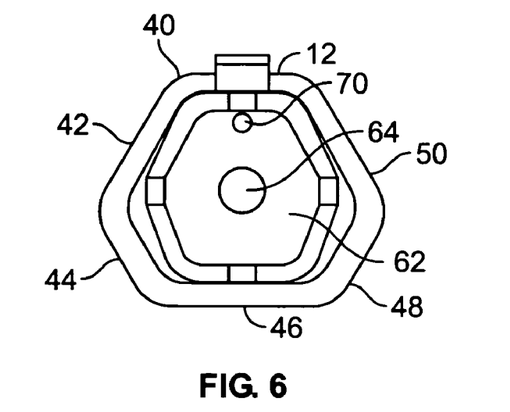
FIG. 6 is an elevational view of the second end of the body of the present needle-stick protector.
Figure 8:
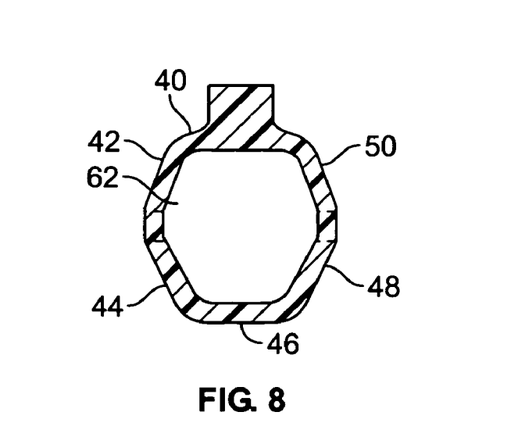
FIG. 8 is a cross-sectional view taken along 7-7 of FIG. 4.

Referring to FIGS. 6, 7, and 8, the side walls 40-50 define the interior space 62 extending between the first and second ends 14 and 16 of the body 12. As shown in FIG. 7, an opening 64 for the needle 76 and an opening 70 for a wire 120 are defined by the body 12 at the first end 14. The opening 70 for a wire 120 is shown in FIG. 7 as circular, but the opening 70 may be of any geometric configuration, such as square, rectangular, or polygonal. The opening may also be a V-shaped opening. The threads 20 on the interior walls of the first end 14 of the body 12 mate with threads (not shown) on the connection end 22 of the catheter hub 18 to form a luer lock engagement 180 between the needle-stick protector 10 and the catheter hub 18.

Figures 1A, 1B:
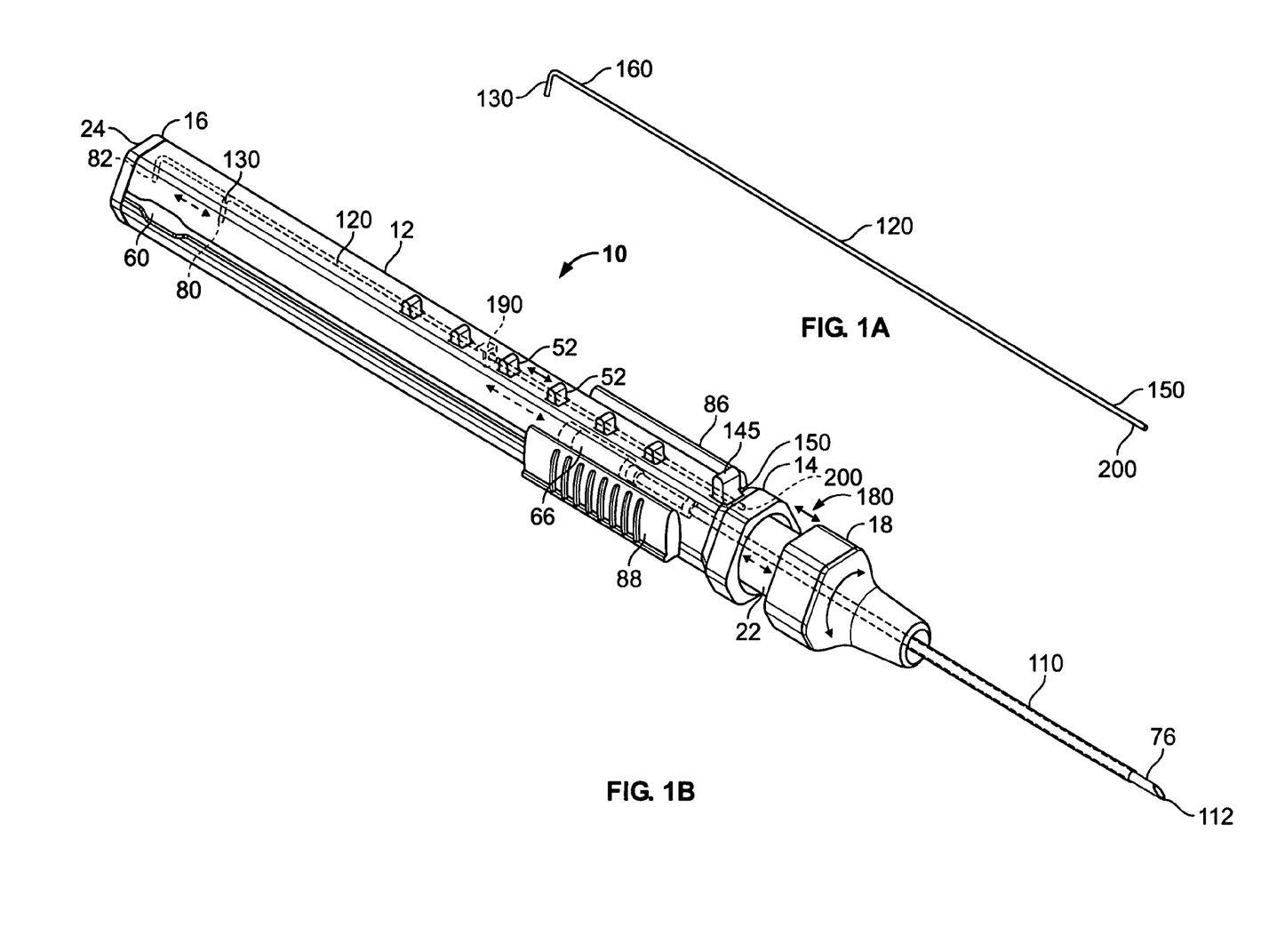
FIG. 1A shows a safety feature component of the present invention.
FIG. 1B is a perspective view of a needle-stick protector according to an embodiment of the present invention attached to a catheter hub.
Figure 1C:
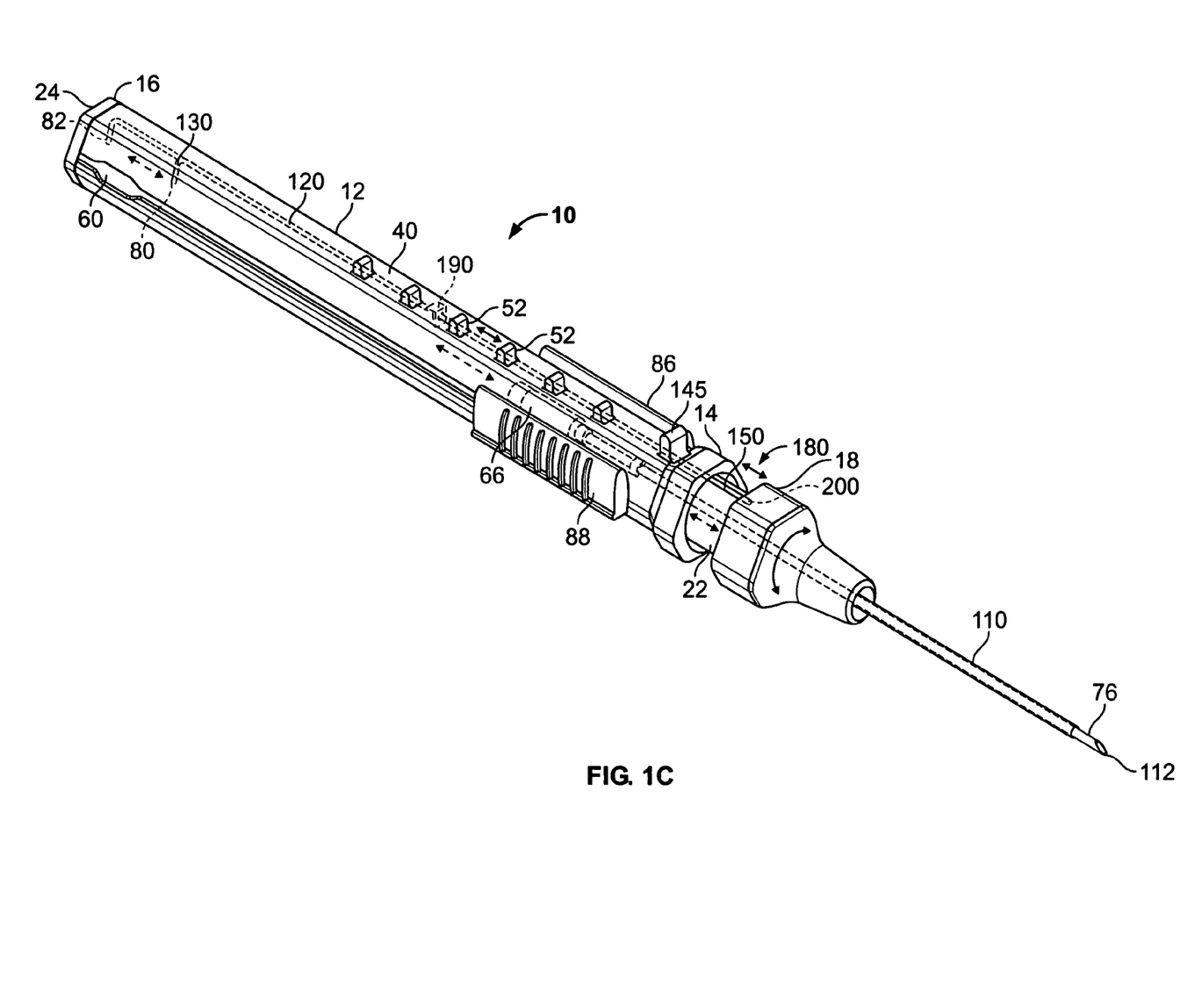
FIG. 1C is a perspective view of a needle-stick protector according to another embodiment of the present invention attached to a catheter hub.

As shown in FIG. 1A, the safety feature component of the present invention includes a wire 120 having a first end 150 and a second end 160. The second end 160 of the wire 120 forms an L-shaped pin 130 and the first end 150 of the wire 120 forms a locking pin 200. FIGS. 1B and 1C illustrate embodiments of the safety feature component of the present invention in a needle-stick protector.

Referring to FIGS. 1B, 5, and 7, the wire 120 extends along the interior space 62 of the body 12 of the needle-stick protector 10. The interior space 62 of the body 12 contains a bracket 190 for holding the wire 120 parallel to the sidewall 40 of the body 12. The wire 120 is restrained in this way so to disallow intentional or inadvertent disengagement of the wire 120 until the needle hub 66 is locked back in position 82. The L-shaped pin 130 at the second end 16 of the body 12 is positioned adjacent to first and second locking positions 58 and 60, respectively. When the needle 76 is located in the catheter, the L-shaped pin 130 is in a first position 80. When the needle 76 is fully retracted and locked in the body of the needle-stick protector, the L-shaped pin 130 is in a second position 82. According to an embodiment of the present invention, illustrated in FIGS. 1B and 7, the first end 150 of the wire 120 exits through an opening 70 in the first end 14 of the body 12 and slightly penetrates the luer lock engagement 180, terminating at about 0.025 to about 0.100 inch, preferably about 0.050 inch into the luer lock engagement 180. At this position, the first end 150 of the wire 120 forms a locking pin 200 which prevents any movement in the luer lock engagement 180.

According to a further embodiment of the present invention, illustrated in FIGS. 1C and 7, the first end 150 of the wire 140 exits through an opening 70 in the first end 14 of the body 12 and extends through the luer lock engagement 180, terminating at about 0.010 to about 0.050 inch, preferably about 0.025 inch into the catheter hub 18, but not penetrating the interior chamber of the catheter hub (not shown). As in FIG. 1*b*, in this position, the first end 150 of the wire 120 also forms a locking pin 200 which prevents any movement in the luer lock engagement 180.

Referring to FIGS. 1B, 1C, and 2, the operation and intended use of the needle protector 10 will now be described. As shown in FIGS. 1B and 1C, the catheter hub 18 includes a catheter 110. The needle hub 66 is positioned adjacent the first end 14 of the body 12. When the needle hub 66 is so positioned, the needle 76, which includes a pointed end 112, extends through the catheter hub 18 and the catheter 110. When the catheter 110 is to be inserted into the blood vessel of a patient (not shown), the needle protector 10 is moved to the side of the blood vessel. The user of the needle protector 10 grips the body 12 and places his or her middle finger on the first wall 40 and thumb on the second handle 88. The index finger engages the first projection or tab 145 so that the body 12 can be accurately positioned with respect to the blood vessel. When the pointed end 112 of the needle 76 is properly positioned, the user of the needle protector 10 pushes the pointed end of the needle 112 into the blood vessel. Insertion of the needle 76 into the blood vessel results in the insertion of the catheter 110 into the blood vessel.

After the catheter 110 has been inserted into a blood vessel, the user of the needle protector 10 uses his or her thumb and middle finger to engage the first and second handles 86 and 88 of the needle hub 66. The grips 102 prevent slippage by the user. The user pulls back on the first and second handles 86 and 88 thereby causing the needle hub 66 to move from proximal the first end 14 to proximal the second end 16 of the body 12. The first and second handles 86 and 88 move along the first and second slots 54 and 56, respectively, to guide the needle hub 66 along its predetermined path. Movement of the needle hub 66 causes corresponding movement of the needle 76, thereby withdrawing it from the patient's blood vessel. As the needle hub 66 moves toward the second end 16 the needle 76 passes through the needle opening 64 into the interior space 62 of the body 12 as shown in FIG. 7.

As the needle hub 66 moves along the interior space 62 of the body 12, it encounters the L-shaped pin 130 at the second end 16 of the body 12. The engagement of the needle hub 66 with the L-shaped pin 130 causes the L-shaped pin 130 to move from a first position 80 to a second position 82 as the needle hub 66 moves into the locking positions 58 and 60. Movement of the L-shaped pin 130 from the first position 80 to a second position 82 causes the wire 120 to move towards the second end 16 of the body and causes the first end 150 of the wire 120 to disengage from the luer lock engagement 180. Disengagement of the locking pin 200 from the luer lock engagement 180 unlocks the luer lock engagement 180, allowing the user to freely move the luer lock engagement 180 and disengage the needle-stick protector 10 from the catheter hub 18 but only after the needle 76 is securely locked into the body 12 of the needle-stick protector 10. The catheter hub 18 can then be used as intended.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

What is claimed is:

1. A needle-stick protector for an intravenous catheter, comprising:
    a body having a first end and a second end, the body including a plurality of side walls extending between the first and second ends in a geometric configuration, the side walls defining an interior space and a first slot and a second slot, said slots each having a single locking portion adjacent to said second end;
    a needle hub positioned in the interior space of the body, the needle hub having a front end, a back end, a first side and a second side, the front end being adapted to receive a needle, the first and second sides each including a handle, the handle extending through the slots to positions outside of the body and consisting of a handle member, the handle member having at least one locking projection on the interior surface;
    a needle in communication with the front end of the needle hub, whereby movement of the needle hub from the first end to the second end results in corresponding movement of the needle into the body until the locking projection of the handle member irreversibly engages said locking portion, locking the needle in a fully retracted position with the handle; and
    a locking pin extending through the leur lock engagement and penetrating the catheter hub to prevent movement of a leur lock engagement that connects the needle-stick protector to a catheter hub until the needle is securely locked in the body.

2. A needle-stick protector for an intravenous catheter, comprising:
    a body having a first end and a second end, the body including a plurality of side walls extending between the first and second ends in a geometric configuration, the side walls defining an interior space and a first slot and a second slot, said slots each having a single locking portion adjacent to said second end;

a needle hub positioned in the interior space of the body, the needle hub having a front end, a back end, a first side and a second side, the front end being adapted to receive a needle, the first and second sides each including a handle, the handle extending through the slots to positions outside of the body and consisting of a handle member, the handle member having at least one locking projection on the interior surface;

a needle in communication with the front end of the needle hub, whereby movement of the needle hub from the first end to the second end results in corresponding movement of the needle into the body until the locking projection of the handle member irreversibly engages said locking portion, locking the needle in a fully retracted position with the handle; and a locking pin and a wire extending along the interior space of the body connecting an L-shaped pin at the second end of the body to the locking pin to prevent movement of a leur lock engagement that connects the needle-stick protector to a catheter hub until the needle is securely locked in the body.

3. The needle-stick protector for an intravenous catheter of claim 2, wherein the L-shaped pin moves from a first position to a second position when the needle hub engages the L-shaped pin.

4. The needle-stick protector for an intravenous catheter of claim 2, wherein the wire moves towards the second end of the body when the L-shaped pin moves from a first position to a second position.

5. The needle-stick protector for an intravenous catheter of claim 4, wherein the locking pin disengages from the leur lock engagement when the L-shaped pin moves from a first position to a second position.

6. A needle-stick protector for an intravenous catheter of claim 1 further comprising a cap located at the second end of the body.

7. A needle-stick protector, comprising:

a body having a first end, a second end having a cap, and at least one handle, with the body defining a plurality of openings adjacent the second end;

a needle hub including a plurality of locking means, the locking means being received by the openings to lock the needle hub into adjacent said second end and wherein the handle is at least partly covered by and locked into said cap: and means comprising a locking pin at the first end of the body that prevents movement of the luer lock engagement and a wire extending along the interior space of the body connecting an L-shaped pin at the second end of the body to the locking pin at the first end of the body to prevent movement of a leur lock engagement that connects the needle-stick protector to a catheter hub until the handle is at least partly covered by and locked into said cap.

8. The needle-stick protector for an intravenous catheter of claim 7, wherein the L-shaped pin moves from a first position to a second position when the needle hub engages the L-shaped pin.

9. The needle-stick protector for an intravenous catheter of claim 7, wherein the wire moves towards the second end of the body when the L-shaped pin moves from a first position to a second position.

10. The needle-stick protector for an intravenous catheter of claim 7, wherein the locking pin disengages from the luer lock engagement when the L-shaped pin moves from a first position to a second position.

* * * * *